US006004272A

United States Patent [19]

Barry et al.

[11] Patent Number: 6,004,272

[45] Date of Patent: Dec. 21, 1999

[54] ULTRASONIC BONE TESTING APPARATUS WITH REPEATABLE POSITIONING AND REPEATABLE COUPLING

[75] Inventors: Donald Barry, Norwood; Richard E. Cabral, Tewksbury; Daniel W. Hawkins, Gardner; Dennis G. Lamser, Arlington; John P. O'Brien, Brookline; Jay A. Stein, Farmingham; Kevin E. Wilson, Cambridge, all of Mass.

[73] Assignee: Hologic, Inc., Waltham, Mass.

[21] Appl. No.: 08/477,580

[22] Filed: Jun. 7, 1995

[51] Int. Cl.$^{6}$ .......................... A61B 8/00

[52] U.S. Cl. .......................... 600/449

[58] Field of Search .......................... 128/660.01, 660.02, 128/660.06, 661.03; 73/597, 599; 600/437, 438, 442, 449

[56] References Cited

U.S. PATENT DOCUMENTS

| | | | |
|---|---|---|---|
| Re. 32,782 | 11/1988 | Pratt, Jr. | 128/661.03 |
| 3,345,863 | 10/1967 | Henry et al. . | |
| 3,477,422 | 11/1969 | Jurist et al. . | |
| 3,713,329 | 1/1973 | Munger . | |
| 4,062,355 | 12/1977 | Kaye . | |
| 4,304,055 | 12/1981 | Hanson . | |
| 4,361,154 | 11/1982 | Pratt, Jr. | 128/661.03 |
| 4,421,119 | 12/1983 | Pratt, Jr. | 128/661.03 |
| 4,594,895 | 6/1986 | Fujii . | |
| 4,669,482 | 6/1987 | Ophir . | |
| 4,679,565 | 7/1987 | Sasaki . | |
| 4,680,966 | 7/1987 | Nicolas . | |
| 4,774,959 | 10/1988 | Palmer et al. | 128/661.03 |
| 4,913,157 | 4/1990 | Pratt, Jr. et al. | 128/661.03 |
| 4,926,870 | 5/1990 | Brandenburger . | |
| 4,930,511 | 6/1990 | Rossman et al. . | |
| 4,941,474 | 7/1990 | Pratt, Jr. | 128/661.03 |
| 4,976,267 | 12/1990 | Jeffcott et al. . | |
| 5,014,970 | 5/1991 | Osipov | 128/661.03 |
| 5,025,789 | 6/1991 | Hassler | 128/661.03 |

FOREIGN PATENT DOCUMENTS

| | | |
|---|---|---|
| 8002796 | 12/1980 | European Pat. Off. . |
| 0299906 | 1/1989 | European Pat. Off. . |
| 0312847 | 4/1989 | European Pat. Off. . |
| 0341969 | 11/1989 | European Pat. Off. . |
| 0516353 | 12/1992 | European Pat. Off. . |
| 0570936 | 11/1993 | European Pat. Off. . |
| 0576217 | 12/1993 | European Pat. Off. . |
| 0663182 | 7/1995 | European Pat. Off. . |
| 2257253 | 1/1993 | United Kingdom . |
| WO9325146 | 12/1993 | WIPO . |

OTHER PUBLICATIONS

"The measurement of broadband ultrasonic attenuation in cancellous bone", Langton et al., MEP Ltd. 1984 vol. 13 No. 2, pp. 89–91.

(List continued on next page.)

*Primary Examiner*—Francis J. Jaworski
*Attorney, Agent, or Firm*—Cooper & Dunham LLP

[57] ABSTRACT

An ultrasonic bone testing apparatus has a foot well assembly and a shin guide assembly which are mechanically coupled to secure a foot and lower leg of patient. The shin guide assembly includes a molded form lined with contoured foam lining. An instep support guide having sliding blocks is mounted on the molded form. The sliding blocks attach the shin guide assembly to the foot well assembly. The apparatus further includes a transducer drive mechanism for positioning a pair of transducer assemblies. A controller automatically modifies the positioning of the transducer assemblies until ultrasonic coupling is achieved and a receiving transducer receives a signal of a predetermined quality. The distance between the transducers is continuously measured by a position encoder. The controller uses temperature readings from a temperature sensor to improve the accuracy of the position encoder measurements and correct for temperature dependent inaccuracy in the ultrasound measurement. A coupling pad and acoustical delay line of the transducer assembly provide a waveguide function to collimate an acoustical beam. The elastomer coupling pad has an angled surface which expels air bubbles from a contact area when pressure is applied to the pad.

19 Claims, 12 Drawing Sheets

2 42 40 41 20 1 51 31 30 50 61 3 60 37

U.S. PATENT DOCUMENTS

| | | | |
|---|---|---|---|
| 5,038,787 | 8/1991 | Antich et al. . | |
| 5,042,489 | 8/1991 | Wiener et al. . | |
| 5,054,490 | 10/1991 | Rossman et al. . | |
| 5,099,849 | 3/1992 | Rossman et al. . | |
| 5,134,999 | 8/1992 | Osipov | 128/661.03 |
| 5,143,069 | 9/1992 | Kwon et al. . | |
| 5,143,072 | 9/1992 | Kantorovich et al. . | |
| 5,197,475 | 3/1993 | Antich et al. . | |
| 5,218,963 | 6/1993 | Mazess . | |
| 5,228,445 | 7/1993 | Pak et al. . | |
| 5,259,384 | 11/1993 | Kaufman et al. . | |
| 5,309,898 | 5/1994 | Kaufman et al. . | |
| 5,335,661 | 8/1994 | Koblanski | 128/661.03 |
| 5,343,863 | 9/1994 | Wiener et al. . | |
| 5,349,959 | 9/1994 | Wiener et al. . | |
| 5,361,767 | 11/1994 | Yukov . | |
| 5,396,891 | 3/1995 | Whitney et al. . | |
| 5,426,979 | 6/1995 | Kantorovich et al. . | |
| 5,433,203 | 7/1995 | Kimura et al. . | |
| 5,452,722 | 9/1995 | Langton | 128/660.06 |
| 5,458,130 | 10/1995 | Kaufman et al. . | |
| 5,483,965 | 1/1996 | Weiner et al. . | |

OTHER PUBLICATIONS

IGEA, DBM Sonic 1200 Brochure (undated).

"Bone" Official Journal of the International Bone and Mineral Society, vol. 16, No. 1, pp. 246–249 Jan. 1995.

Ultrasound Assessment of Bone Fragility in the Climacteric Women by DBM Sonic 1200, Mura Marta.

Perth International Bone Meeting, Bone Fragility in the Year 2000, p. 65 (Feb. 1995).

Connective Tissue Changes in the Menopause, M. Brincat et al.

Minhorst Osteoson brochure (May 1995).

Minhorst Osteoson K IV brochure (undated).

Ultrasound for Bone Measurement, A Private Symposium, Lunar, Apr. 1992.

Lunar, Achilles Ultrasound Bone Densitometer brochure (undated).

Clinical Investigations, "Preliminary Evaluation of a New Ultrasound Bone Densitometer" by Belinda Lees and John C. Stevenson, Calif Tissue Int. 1993.

Report on "Ultrasonic Assessment of Bone III", May 1993.

Observations at ASBMR, by G.H. Brandenburger, 1991.

"Ultrasound Measurements of the Os Calcis", by R. Mazess et al., Presented at the Third Bath Conference of Osteoporosis and Bone Mineral Measurement (Jun. 1992).

Perth International Bone Meeting, Bone Fragility in the Year 2000: Clinical Measurement, p. 63 (Feb. 1995).

Perth International Bone Meeting, Bone Fragility in the Year 2000: Clinical Measurement, p. 61 (Feb. 1995).

1
2
3
20
30
31
37
40
41
42
50
51
60
61

40
20

50
60
61

36
106
102
110
109
101
103
104
105

ULTRASONIC BONE TESTING APPARATUS WITH REPEATABLE POSITIONING AND REPEATABLE COUPLING

BACKGROUND OF THE INVENTION

1. Field of the Invention

This invention relates to the field of ultrasonic analysis of bone tissue in humans, and more particularly to an apparatus using novel techniques for reproducibly measuring certain properties of the heel bone or os calcis using transmission and reflection of ultrasonic energy.

2. Description of Related Art

Certain known techniques for measuring properties of the heel bone or os calcis have required that the foot is held between a pair of ultrasonic transducers in a jig or clamp while the foot and the ultrasonic transducers are immersed in a water bath to couple the ultrasonic energy between the transducers and the foot. These immersing procedures reduce interference with the coupling of ultrasonic energy which is caused by air or other gas present between the transducer and the object to be tested. However, the techniques are relatively time consuming and can be inconvenient.

Other previous designs of ultrasonic bone testing apparatus include a support behind the leg in the calf muscle area. The use of a footrest allows some tolerance for the positioning of the foot. However, the approach has the disadvantage that the footrest does not facilitate consistent measurement because the size and location of calf muscles can vary greatly. In addition, the patient's calf muscle tends to be flaccid while the patient is sitting, and therefore does not provide a fixed reference surface even for the same person during subsequent measurements.

OBJECTS AND SUMMARY OF THE INVENTION

Accordingly, it is an object of this invention to provide an improved ultrasonic bone analysis apparatus.

Another object of this invention is to provide an ultrasonic bone analysis apparatus which omits the water bath and replaces the coupling function of the water with a system that includes soft elastomer pads, delay lines, and a mechanism and controller that causes the transducers to couple to the foot in the desirable manner.

A further object of this invention is to provide an ultrasonic bone analysis apparatus that achieves repeatable results by employing both repeatable positioning and repeatable coupling of the transducers with respect to the foot.

In one example of the invention, the repeatable positioning of the foot is accomplished by a mechanism that locates certain anatomical points of the lower leg and restrains motion during the measurement process by using the located anatomical points. The shin bone or tibia is used as one principal reference surface for the lower leg. The tibia typically has only a thin and uniform covering of skin in the anterior direction, no variable muscle tissue, and provides a hard reference surface even on fairly obese persons. The inferior aspect of the foot and the posteria aspect of the os calcis, at the point just below the lower attachment of the Achilles tendon, provide two other reference surfaces for immobilizing the foot at a specified angle. In order to restrain the foot from lateral-medial rotation, the foot instep is restrained and pressed down and to the rear at an angle of about 55 degrees.

The repeatable coupling of the transducers to the foot can be accomplished by controlling the pressure applied between the transducer and the foot, and monitoring the quality of the signal received by the transducer. The quality of the transducer signal is used as feedback information to modulate the pressure applied via a motor. An acoustical delay line is provided to allow the transducer's wavefronts to evolve from the granular near field pattern to a smoother far field pattern before entering the foot. The acoustical and mechanical properties of the elastomer coupling pad are inherently critical to the operation of the invention.

DETAILED DESCRIPTION

Figure 1:
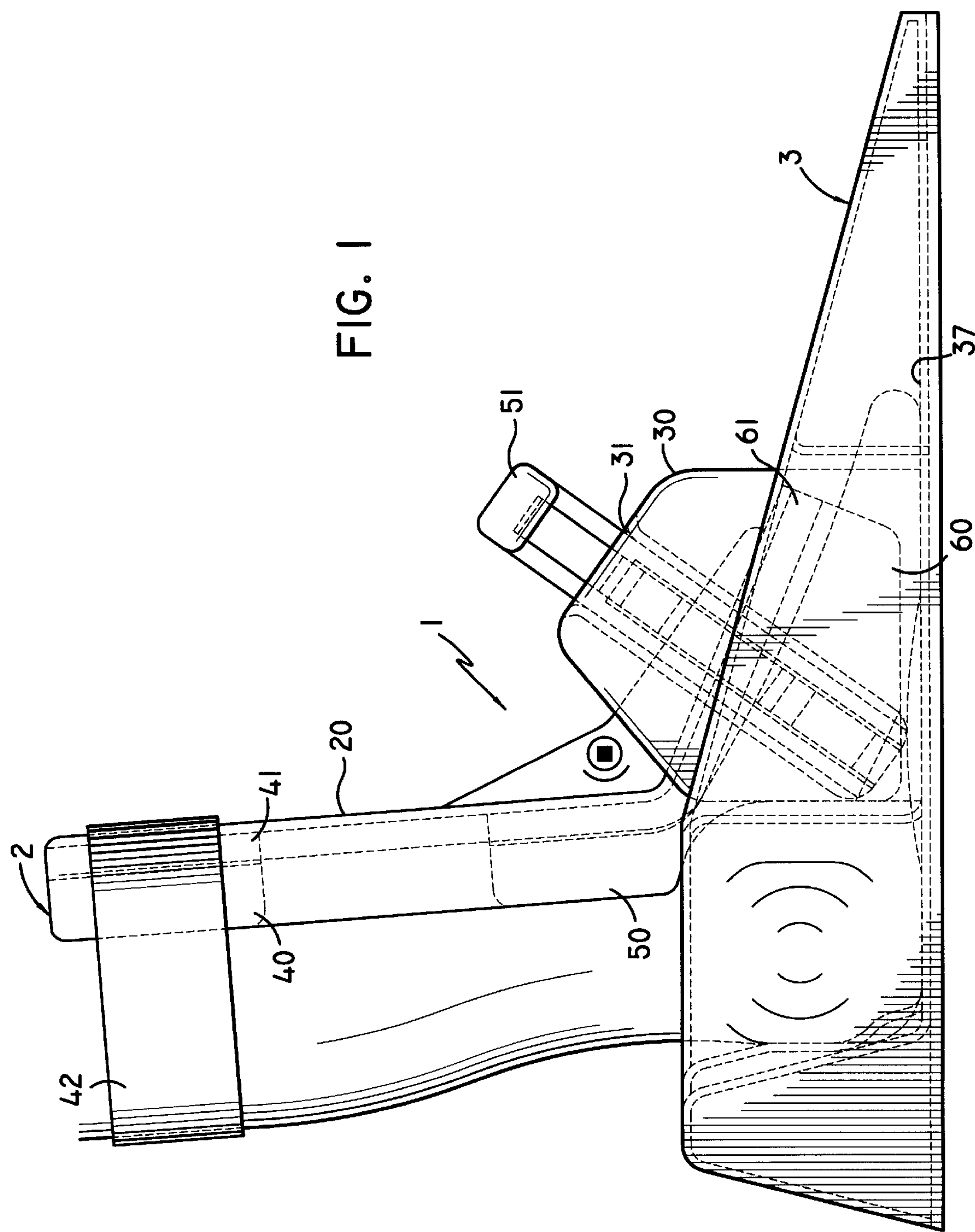
FIG. 1 is a side view of a foot restraint device of the present invention.

Referring to FIG. 1, an ultrasonic bone analysis apparatus according to one embodiment of the invention combines the mechanisms to position and restrain the foot and lower leg into a single foot restraint device 1. The foot restraint device 1 comprises two assemblies, a shin guide assembly 2 and a foot well assembly 3.

Figure 2:
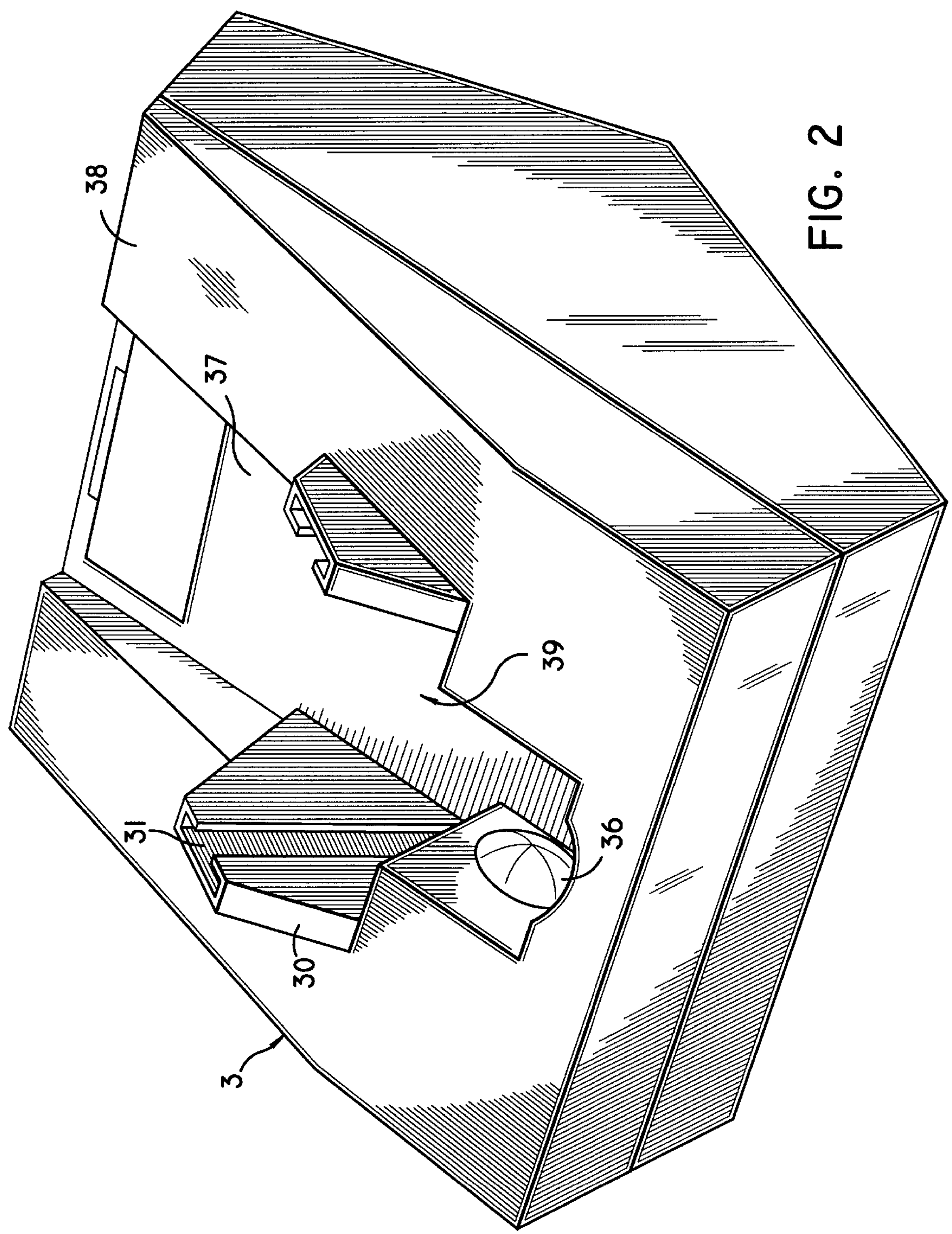
FIG. 2 is a perspective view of a foot well assembly of the present invention.

As seen in FIG. 2, the foot well assembly 3 comprises a box cover 38 having a foot support 39, and foot well bottom 37. The foot support 39 has an area slightly larger than a human foot such that even a large foot can fit comfortably.

Transducer ports 36 are located on the sides of the foot support 39, towards the rear. Bridge brackets 30 with channels 31 are located along the sides of the foot support 39, and are arranged at a predefined angle, preferably 55 degrees, with respect to the foot well bottom 37. The bridge brackets 30 with channels 31 facilitate the mounting of the shin guide assembly 2.

Referring back to FIG. 1, the shin guide assembly 2 includes a plastic molded form 20 lined with contoured foam lining 41. The molded form 20 is a combination of restraints for the shin, instep, and front of the foot into a single piece.

The molded form 20 includes shin restraint section 40 which restrains, supports, and centers the tibia against contoured foam lining 41 with the help of a flexible strap 42 placed around the calf. The flexible strap 42 can be adjusted to secure the molded form 20 comfortably around the patient's leg. The shin restraint section 40 of the shin guide assembly 2 extends upward from an instep support section 50 at an angle of about 95 degrees with respect to the foot well bottom 37 of the foot well assembly 3.

Figure 3:
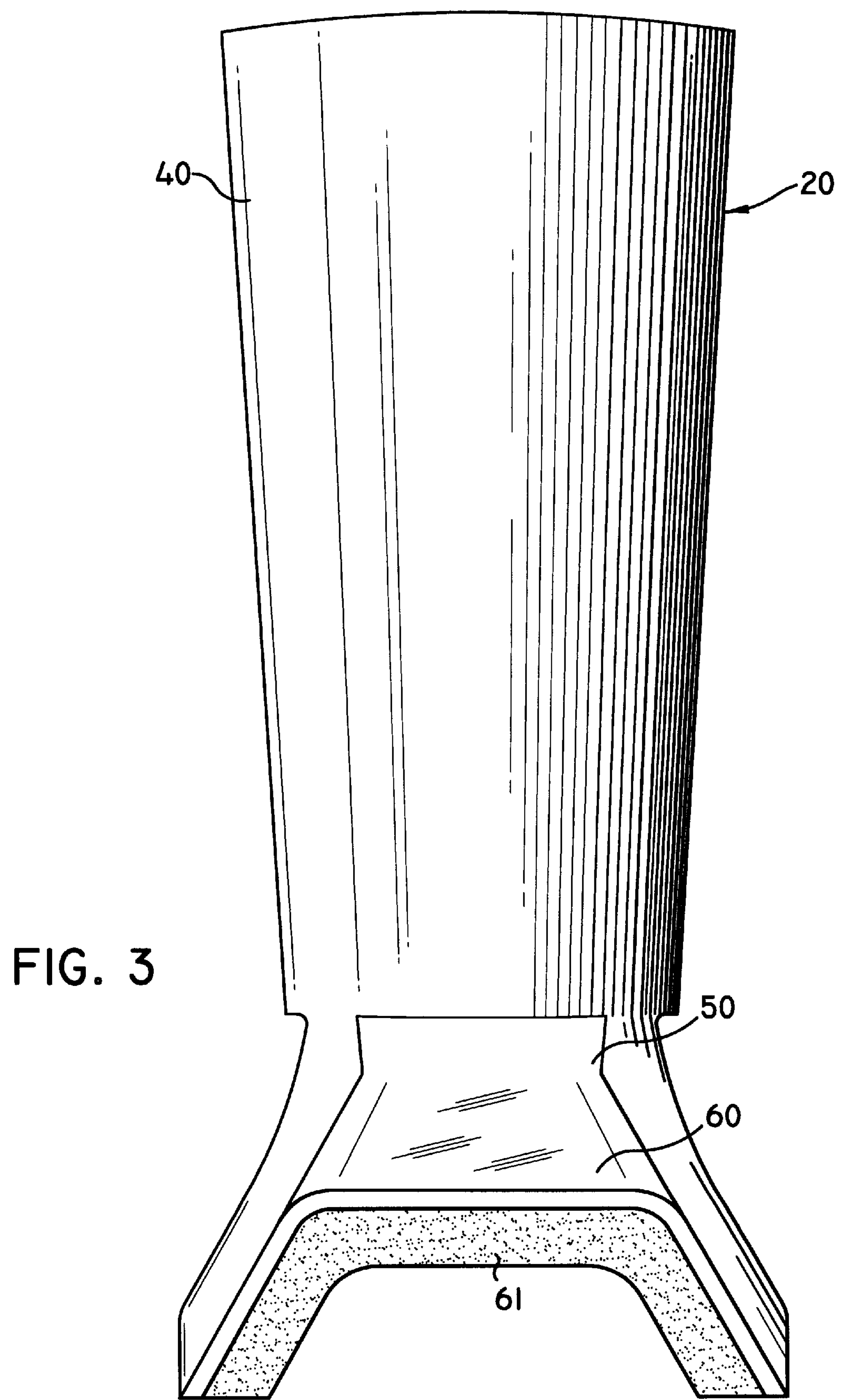
FIG. 3 is a front view of a molded form in a shin guide assembly of the present invention.
Figure 4:
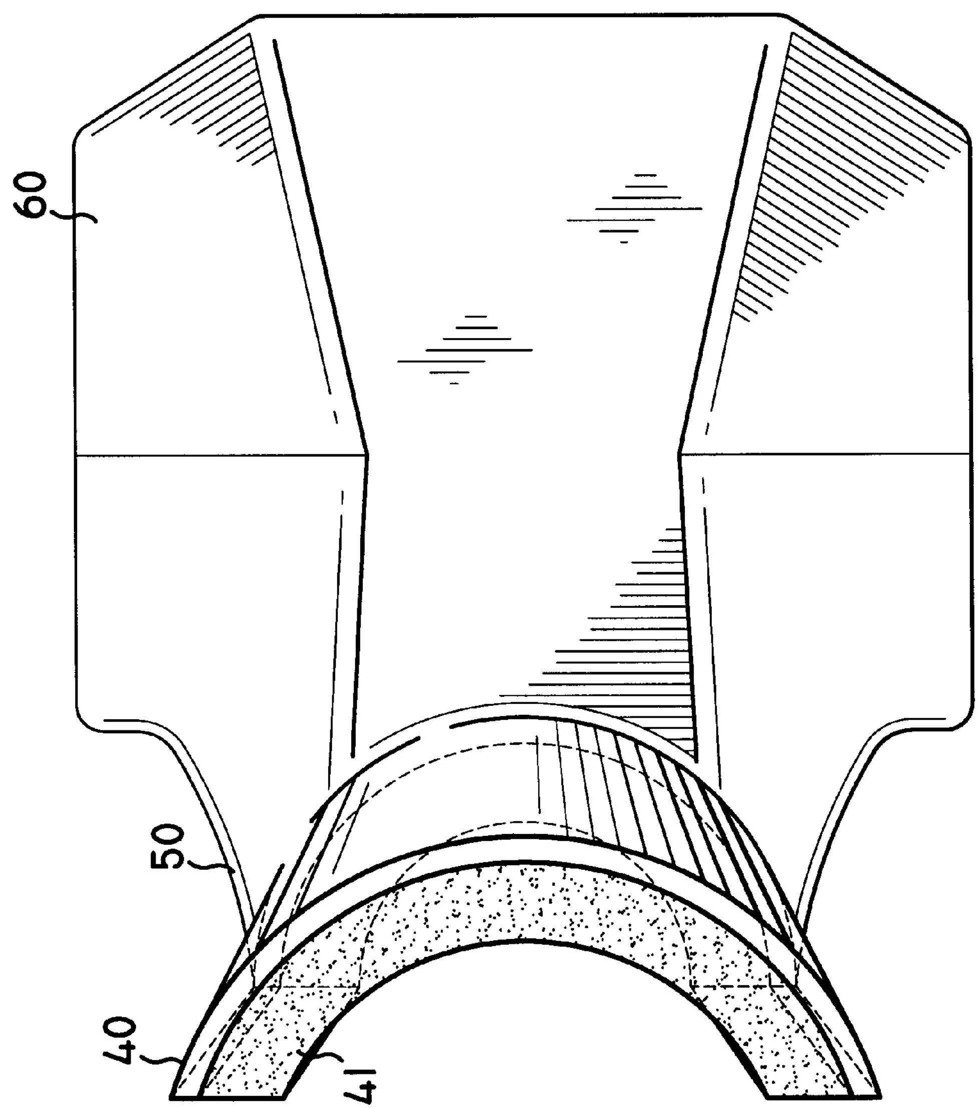
FIG. 4 is a top view of the molded form.
Figure 5:
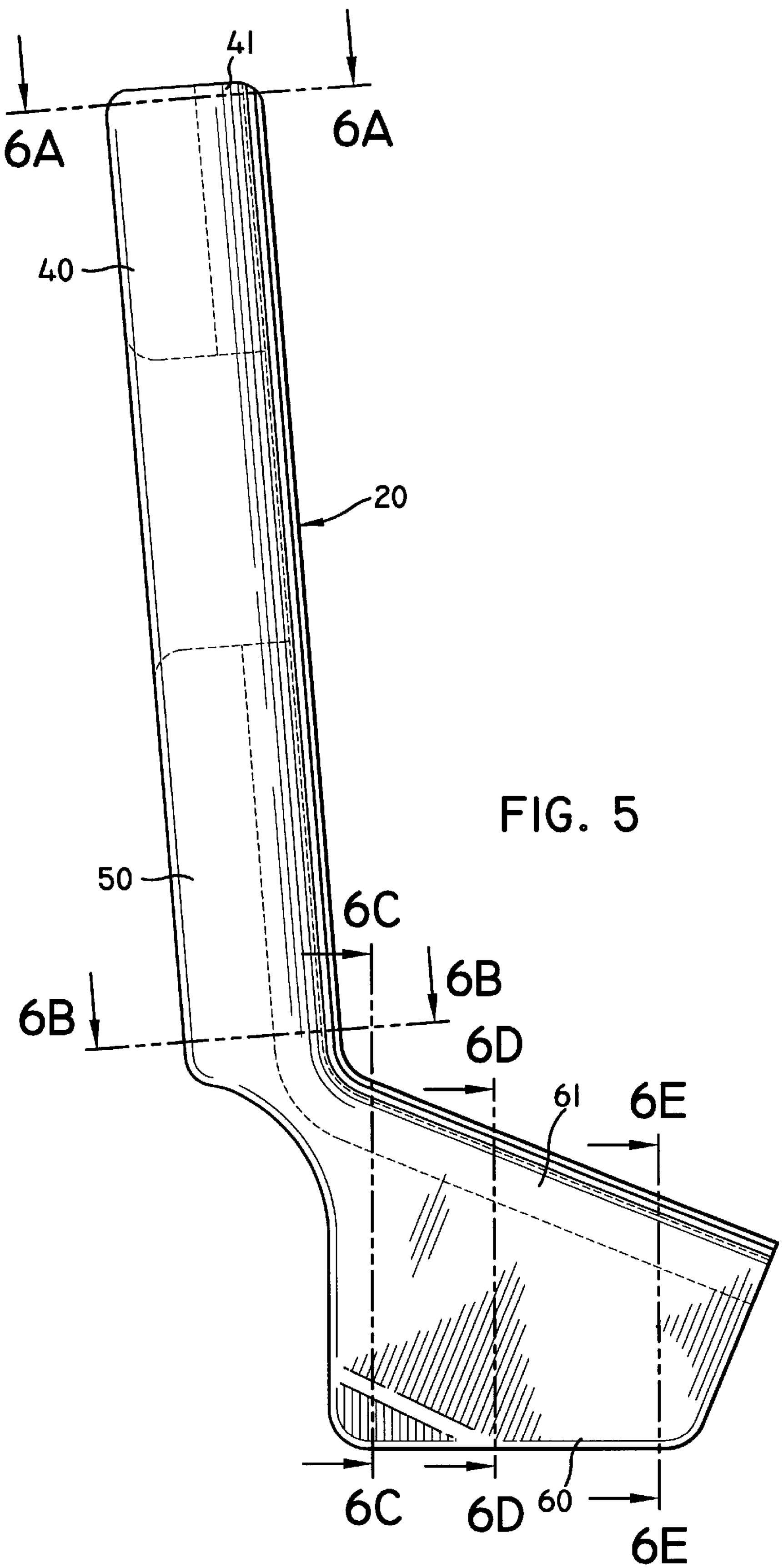
FIG. 5 is a side view of the molded form.
Figure 6A:
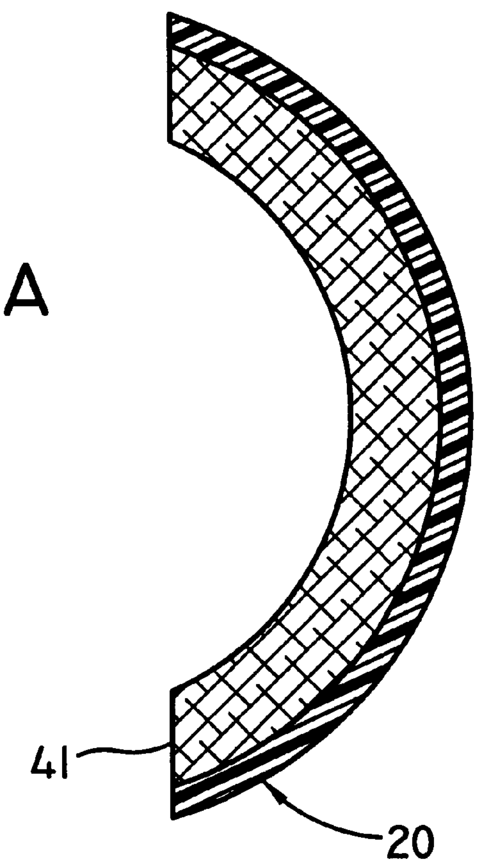
FIG. 6A, FIG. 6B, FIG. 6C, FIG. 6D and FIG. 6E are sectional views of the molded form taken essentially on the lines A—A, B—B, C—C, D—D and E—E, respectively, of FIG. 5.
Figure 6B:
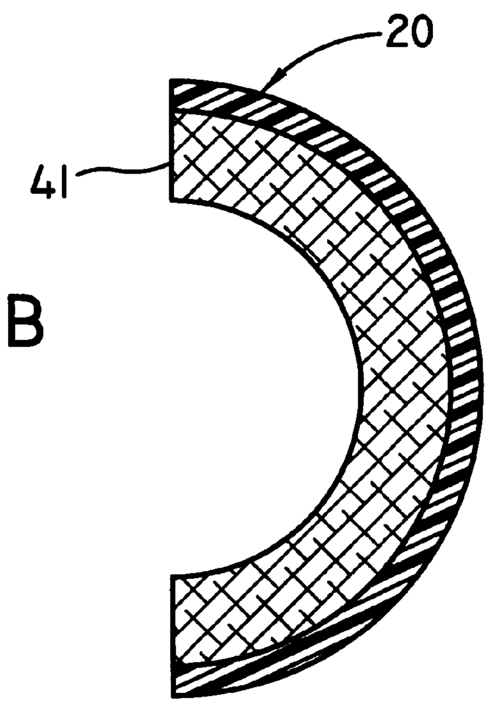

FIG. 3 and FIG. 4 illustrate front and top views of the molded form 20, respectively. The shin restraint section 40 tapers from an upper portion to a lower portion to adapt to the tapering generally found in a human leg from the shin region to the ankle region. For example, referring to FIG. 6A and FIG. 6B which are cross-sectional views of the slices A—A and B—B in FIG. 5, respectively, a cross-section of the shin restraint section 40 near the upper portion has a greater radius than a cross-section of the shin restraint section 40 near the lower portion.

Figure 6C:
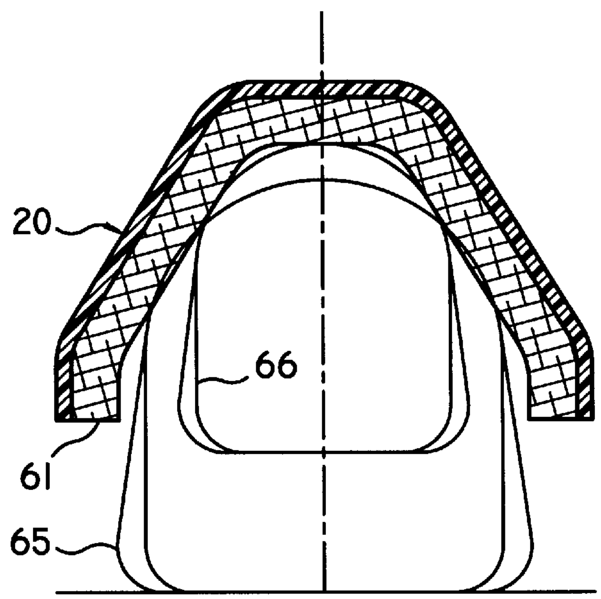
Figure 6D:
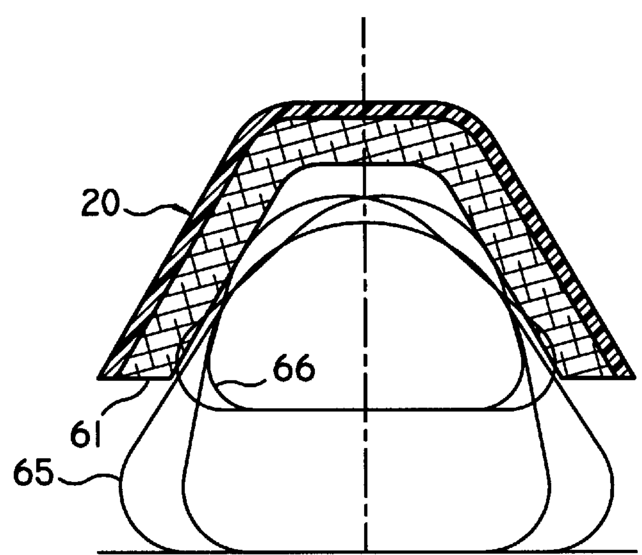
Figure 6E:
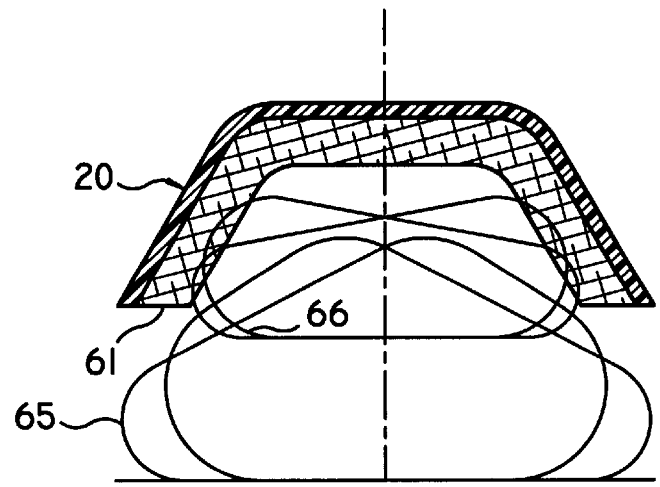

Referring again to FIG. 1, the front of the foot is restrained from lateral rotation by the foot restraint section 60 extending from the lower part of the instep support section 50 towards the toes. As shown in FIG. 3, the foot restraint section 60 has an inverted "U" or "V" shape and includes a contoured foam lining 61 to properly center the front of the foot as the molded form 20 is lowered to match up with the correct width of the foot. The side wall of the foot restraint section 60 and the foot well bottom 37 form a predefined angle which is preferably 60 degrees. Such an arrangement along with contoured foam lining 61 facilitates a comfortable fit over both a large foot 65 and a small foot 66, as shown in FIG. 6C, FIG. 6D and FIG. 6E.

Referring again to FIG. 1, the instep support section 50 includes instep support guide 51. The instep support guide 51 is mounted on opposing sides of the molded form 20, and includes slide blocks 21. The shin guide assembly 2 is attached to the foot well assembly 3 by inserting slide blocks 21 into corresponding channels 31 of the foot well assembly 3. The 55 degree angle of the channels 31 facilitates a proper contact between the instep support guide 51 and the instep area of different size feet, as well as sufficient differential vertical displacement to allow the V-shape of the foot restraint section 60 to match and center varying widths of the lower foot.

Figure 7:
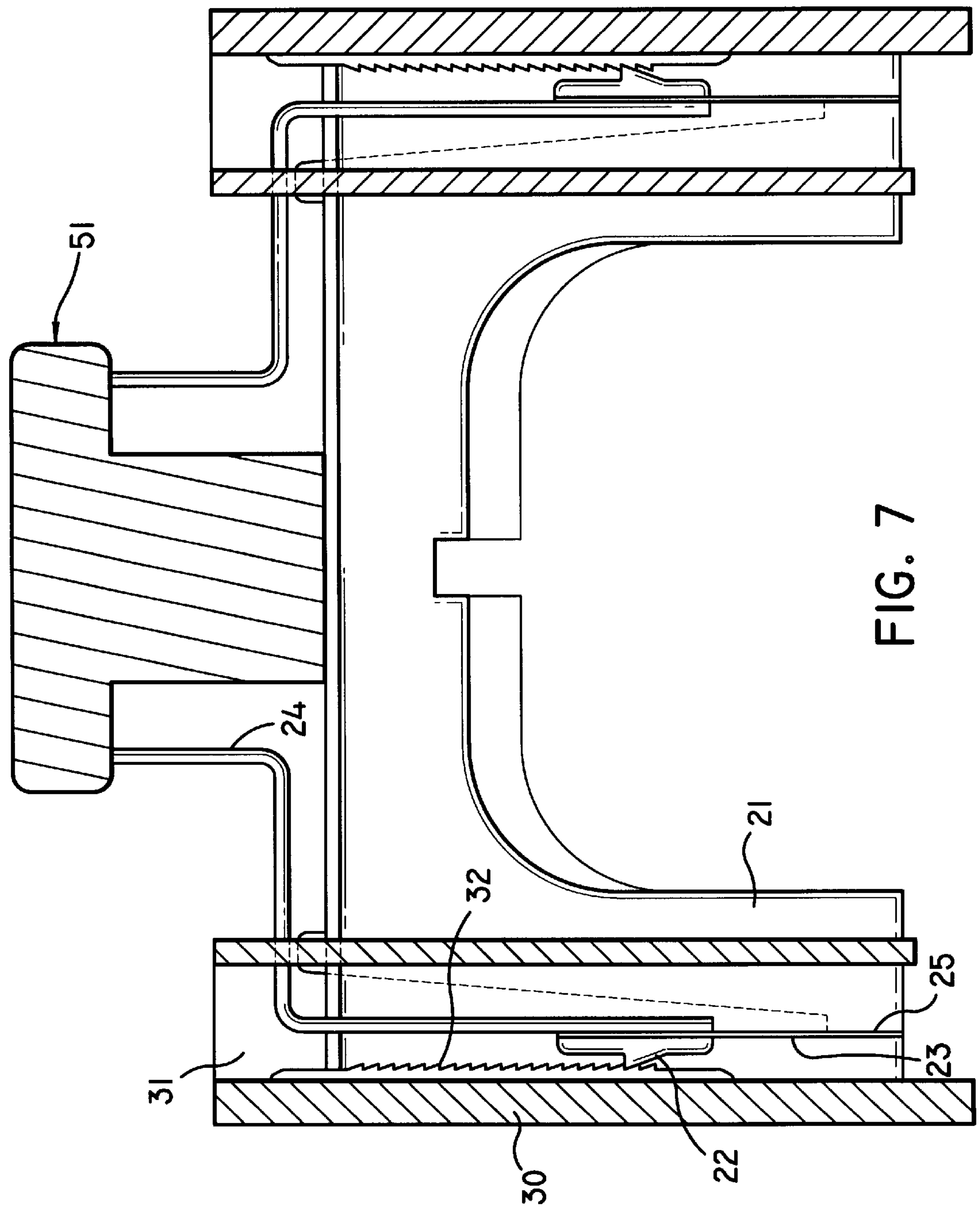
FIG. 7 is a sectional view showing the interaction between bridge brackets with channels of the foot well assembly and slide blocks of an instep support guide.

Referring now to FIG. 7, the channels 31 are lined with strips of repeating triangular ratchet teeth 32, facing downward. The slide blocks 21 have matching ratchet teeth 22 facing upward. When the slide blocks 21 are inserted into the respective channels 31 of the respective bridge brackets 30, the ratcheting action allows the slide block 21 to latch at one of multiple levels to the bridge brackets 30, and thereby the shin guide assembly 2 can be adjusted to fit and restrain comfortably and securely any size foot.

To facilitate release of the mating ratchet teeth 22 and 32 from each other, the ratchet teeth 22 are attached to leaf springs 23 mounted to the base of the slide blocks 21. The operator squeezes together two rigid brackets 24 attached to the free ends of the springs 23, thus retracting the ratchet teeth 22. When the teeth 22 are clear of the teeth 32 inside the channels 31, the operator can pull the slide blocks 21 out of the channels 31 to allow the patient to remove her foot from the foot well 3. The use of ratchet teeth 22 mounted into a spring assembly 25 allows independent optimization of the materials used to provide the spring action, and the materials used to provide the sliding and ratchet action.

The shin guide assembly 2 is conveniently stored for transport of the foot restraint device 1 by sliding the slide blocks 21 into a lowest position in the channels 31.

Figure 8:
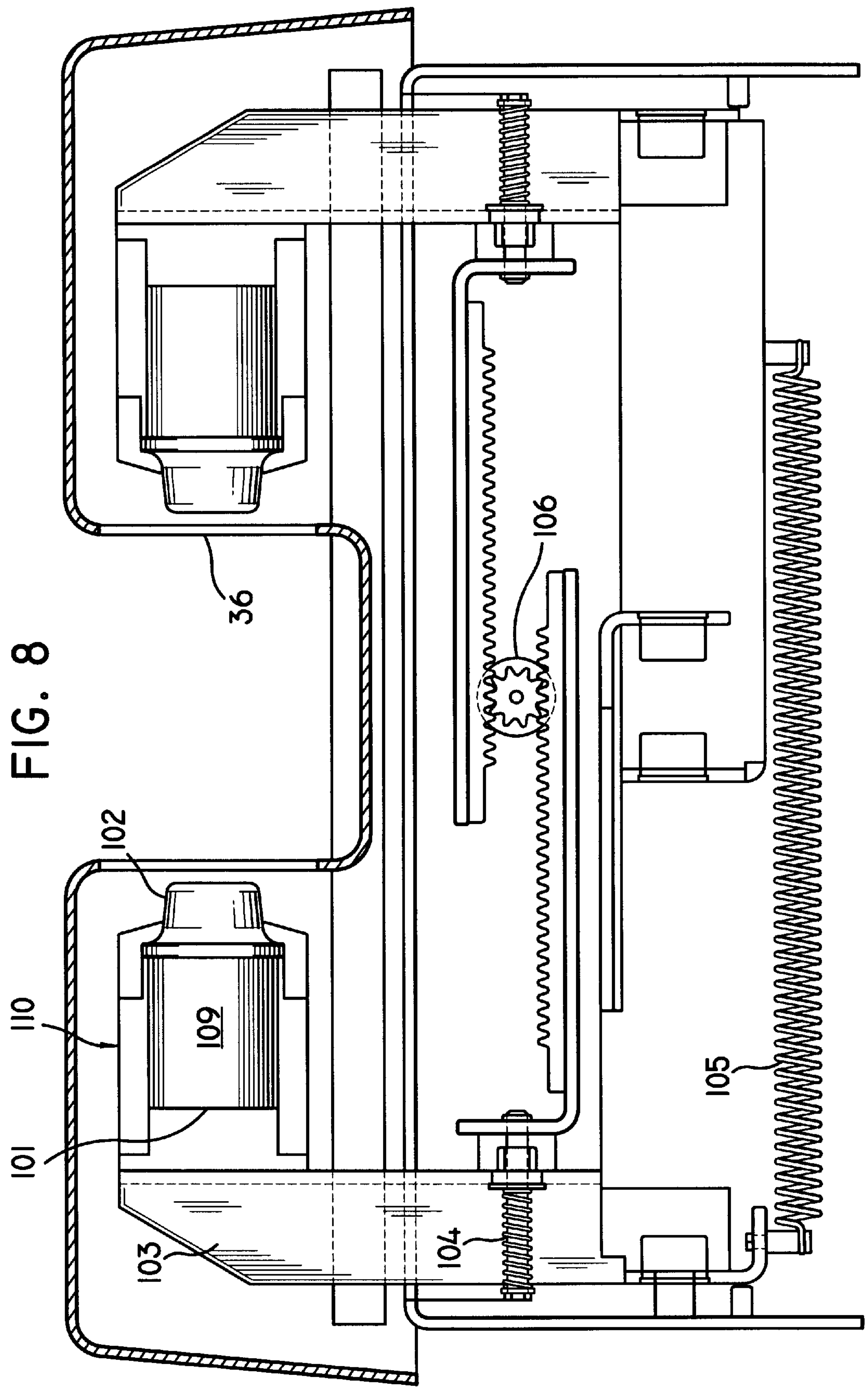
FIG. 8 is a sectional view of a transducer drive mechanism of the present invention.

Referring now to FIG. 8, one embodiment of a transducer drive mechanism of the present invention includes a pair of transducer assemblies 110. The transducer assembly 110 includes transducer 101, acoustical delay line 109 and coupling pad 102.

The transducers 101 are mounted to respective carriages 103 that slide along a lateral-medial axis. Respective compression springs 104 attached to the carriages 103 apply opposing lateral forces towards the center of the foot. The carriage/spring assembly is free floating and will center itself on the foot with equal pressure on both sides.

An extension spring 105 applies the initial pressure when the coupling pads 102 reach the patient's foot. To adjust the pressure in small increments, a stepper motor with rack and pinion mechanism 106 will move a finite number of steps and compress the compression springs 104 that are attached to the respective carriages 103. The compression springs 104 will pull the respective transducers 101 and pads 102 inward at a force proportional to the spring rate and distance translated.

Figure 9B:
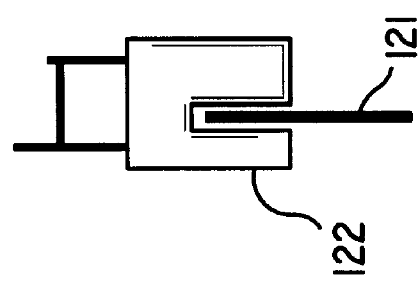
FIG. 9A and FIG. 9B are front and side views of a position encoder of the present invention.
Figure 9A:
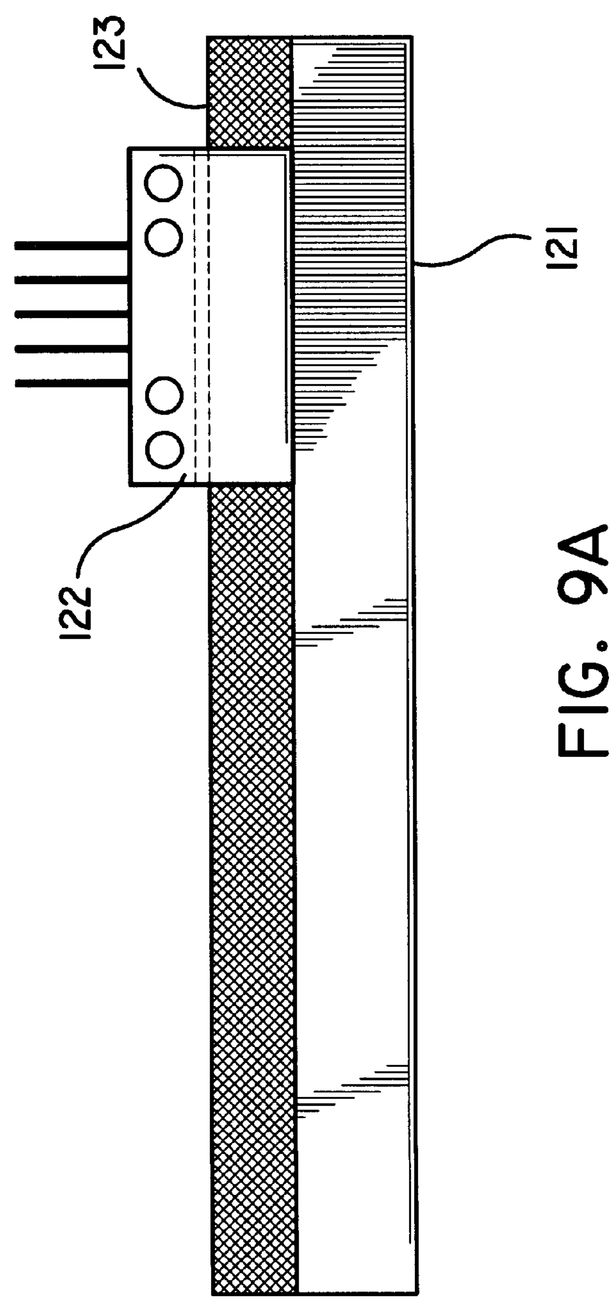

The distance between the transducers 101 is continuously measured by means of a position encoder 120 that is mechanically linked to the motion of the transducers 101. Referring to FIG. 9A and FIG. 9B, front and side views of the position encoder 120, respectively, a preferred encoder uses a code strip 121 mounted onto one of the carriages 103 along with an optical encoder reader 122 mounted on the other of the carriages 103. As the distance between the transducers 101 changes, the code strip 121 moves between the slot of the optical encoder reader 122, and the optical reader 122 reads lines 123 of the code strip 121 as the lines 123 are traversed.

Figure 10:
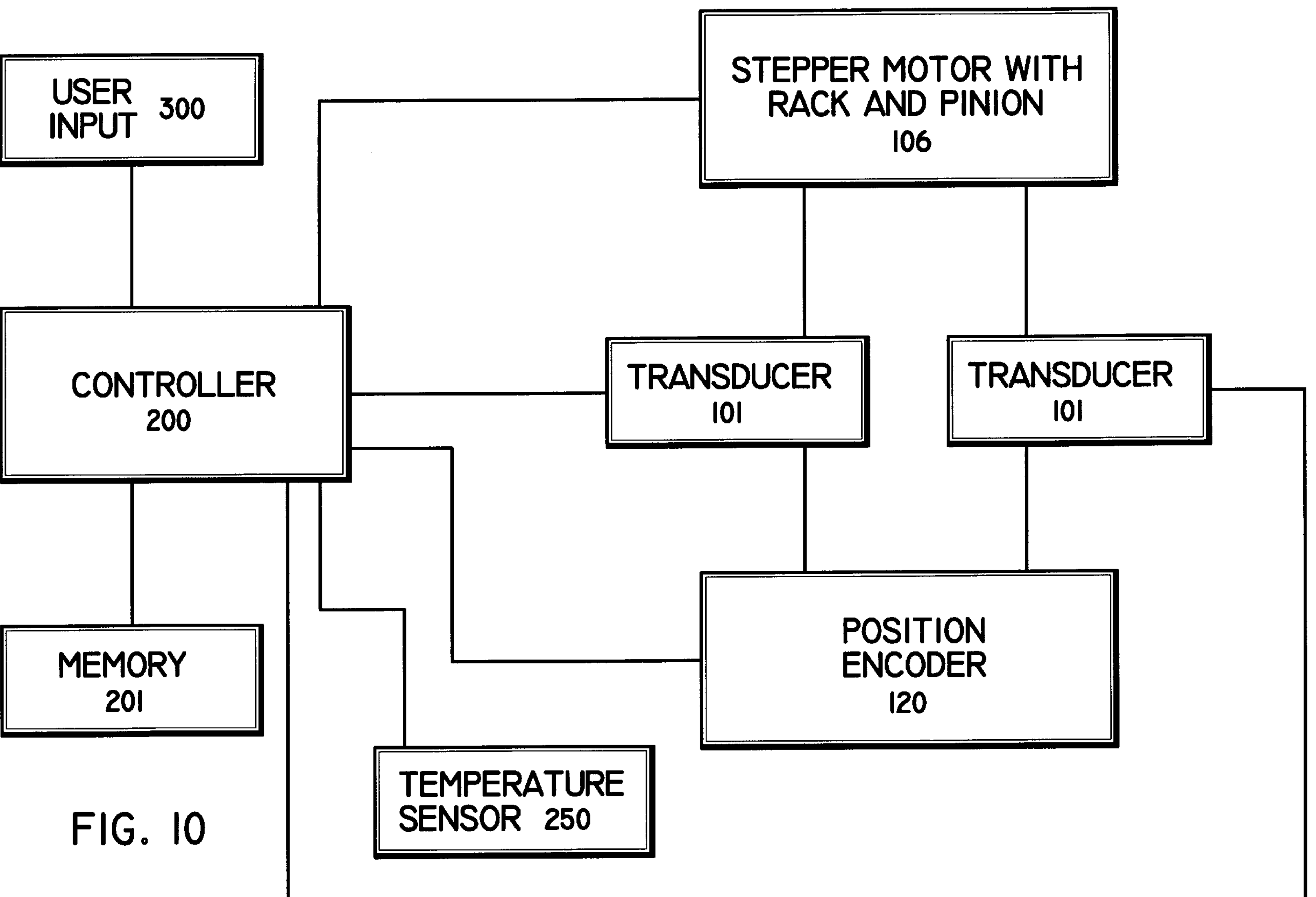
FIG. 10 is a block diagram showing automatic positioning by a transducer drive mechanism of the present invention.

The transducer drive mechanism 100 automatically positions transducer assemblies 110 against the patient's heel with sufficient pressure to insure ultrasonic coupling. The automatic positioning will be explained by referring to FIG. 10. Signals received by the receiving transducer 101 are supplied to controller 200. The controller 200 is preferably a microprocessor-based controller having memory 201 (e.g. RAM and ROM) for storing system and application software and input/output circuitry.

The controller 200 determines the quality of the signals received by the receiving transducer 101 at least in part according to the attenuation of the signals. The controller 200 controls the operations of the stepper motor 106 according to the quality of the signals received by the receiving transducer 101 and positional data supplied by the position encoder 120. The coupling pressure thereby is modified under control of the controller 200 based on the quality of the signals received by the receiving transducer 101. These steps are repeated by the controller 200 until the signals received by the receiving transducer 101 achieve a predetermined quality. Accordingly, the transducer drive mechanism 100 under the control of the controller 200 provides automatic positioning.

The controller 200 determines other parameters of interest, including broadband ultrasound attenuation and bone velocity. Also, the controller 200 calculates a speed of the ultrasonic signals through the foot using the distance between the transducers determined by the position encoder 120. An apparatus for measuring bone characteristics by means of ultrasound is well-known in the art. Such an apparatus is disclosed for example in U.S. Pat. No. 4,774,959 issued to Palmer et al. on Oct. 4, 1988 which is hereby incorporated by reference.

The controller 200 uses temperature readings from temperature sensor 250 to improve the accuracy of the position encoder measurements and correct for temperature dependent inaccuracy in the ultrasound measurement. For example, the controller 200 accounts for linear expansion of the encoder strip 121 by applying a temperature dependent term to the data supplied by the position encoder 120. Additionally, the controller 200 applies a temperature dependent term to correct an estimation of the time delay through the delay line 109 and the coupling pad 102. Furthermore, the controller 200 uses the temperature reading to determine if the apparatus is operating within the specified environmental range allowed, and if not, the operator is informed that the apparatus is not ready to be used.

In addition, guided by operator input 300, the following are examples of additional selectable functions provided by the transducer drive mechanism 100 under the control of controller 200: (1) separate the transducers 101 to allow the foot to be moved to and from a position between the transducers 101 without interference from the transducers; (2) move the position encoder 120 to a known transducer separation zero; (3) extend the transducers 101 to a cleaning or standby position; and (4) secure the transducers 101 in an off or shipping position. The operator input 300 can be any one of the conventional input devices such as pre-allocated buttons, keyboard/keypad device, etc.

Several features of the coupling pads 102 are important to the operation of the described invention. The acoustic impedance of the material of the pads 102 is matched to the acoustic impedance of human skin to provide a minimal loss of power and reduce extraneous reflections. Preferably, the coupling pads are elastomer coupling pads.

The coupling pads 102 also provide a waveguide function to collimate the acoustic beam a sufficient distance along the propagation axis to allow the wavefronts to evolve onto a more uniform intensity pattern. To this end, the acoustical delay lines 109 are provided to allow the wavefronts to evolve from the granular near field pattern to a smoother far field pattern before entering the foot.

The pads 102 are chosen to have a durometer corresponding to a sufficiently flexible waveguide that can partially conform to the shape of a foot and provide some comfort to the patient. The shape of the pads 102 conforms to the heel to eliminate any gaps between the foot and pad. The surfaces of the pads 102 which contact the transducers 101, the delay line 109, or the patent's skin is shaped at an angle to the propagation axis to reduce the acoustic reflection at the pad-to-skin interface by spreading the reflected energy over time and position.

Figure 11C:
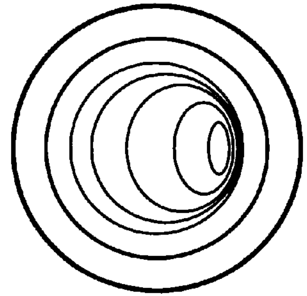
FIG. 11C is a contour diagram of an end of the pad/delay unit.
Figure 11A:
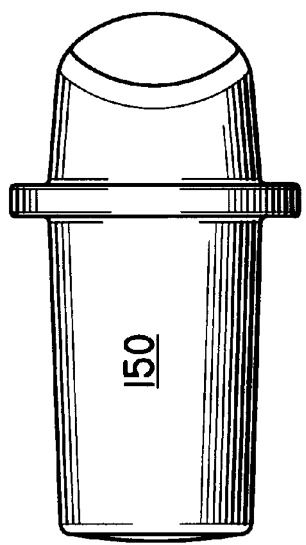
FIG. 11A and FIG. 11B are front and side views of a pad/delay unit of one embodiment of the present invention.
Figure 11B:
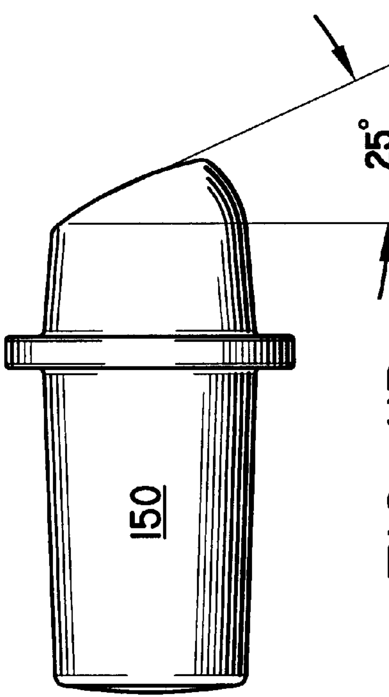

The coupling pad 102 and the delay line 109 are preferably integrated into a single pad/delay unit 150 to reduce an extraneous reflection between a pad-to-delay-line interface. FIG. 11A and FIG. 11B illustrate top and side views of the pad/delay unit 150. The surface of the pad that contacts the patient's skin is shaped to expel air bubbles from the contact area when pressure is applied. FIG. 11C shows the contours of the surface of the pad/delay unit 150 which contacts the patient's skin. The surface preferably forms a 25 degree angle with respect to a vertical axis.

The material of the coupling pad is required to be compatible with coupling gel and non-irritating to the skin. One preferred material is CIBA polyurethane (TDT 178-34) mixed with an additive to provide a cured durometer of approximately 10 to 15 Shore A.

While the elastomer coupling pad is preferred, the coupling pads may be a homogeneous material, a gel pad, or a liquid or gel-filled bladder. The shape of the bladder may be conical whereby air bubbles are expelled when the pad engages the heel.

In a known system, commercially available coupling gel is commonly used between the skin and coupling pads. The commercially available coupling gel is typically water-based. While such water-based gels can be used, a non-aqueous jelly is preferred in this invention. One implementation of the invention uses petroleum jelly as a coupling gel.

The ultrasound coupling gel that is commonly used to efficiently couple ultrasonic energy between the skin and transducers also may be eliminated by using a self-wetting material such as Parker Laboratory Aquaflex pads. In one implementation of the design, self-wetting coupling pads can be used as a disposable, or single use device, eliminating concerns about sanitation.

Having described a preferred embodiment of the invention with reference to the accompanying drawings, it is to be understood that the invention is not limited to that precise embodiment and that various changes and modifications thereof could be effected by one skilled in the art without departing from the spirit or scope of the novel concepts of the invention, as defined in the appended claims.

What is claimed is:

1. An apparatus for performing ultrasonic bone analysis comprising:

a foot well assembly having a foot well for resting a patient's foot and first mating means for connecting to said foot well assembly;

a shin guide assembly for securing a position of said foot in said foot well and a position of a lower leg of said patient, said shin guide assembly having second mating means for mechanically coupling said shin guide assembly to said foot well assembly by connection with said first mating means; and a transducer drive mechanism having a first transducer assembly having a first transducer and a first coupling pad for ultrasonic signals, a second transducer assembly having a second transducer and a second coupling pad for ultrasonic signals, a stepper motor with rack and pinion mechanism for moving said first transducer assembly and said second transducer assembly in predetermined increments, a position encoder for determining relative positions of and distance between said first transducer assembly and said second transducer assembly, a temperature sensor for measuring an ambient temperature, and a controller for positioning said first transducer assembly and said second transducer assembly to apply a pressure against a heel of said patient which achieves ultrasonic coupling, controlling said ultrasonic signals transmitted by one of said first transducer and said second transducer, estimating a time delay through one of said first transducer assembly and said second transducer assembly, applying a temperature dependent term to correct said estimated time delay according to said measured temperature supplied by said temperature sensor, applying a temperature dependent term to position data supplied by said position encoder according to said measured temperature supplied by said temperature sensor, determining a quality of ultrasonic signals received by other of said first transducer and said second transducer, calculating a movement of said first transducer assembly and said second transducer assembly which would modify said coupling pressure to achieve a predetermined quality, and controlling the operation of said stepper motor with rack and pinion mechanism in accordance with at least said calculated movement.

2. An apparatus as set forth in claim 1 wherein said controller calculates a speed of ultrasonic signals through said foot using said distance between said first transducer assembly and said second transducer assembly determined by said position encoder.

3. An apparatus as set forth in claim 1 wherein said position encoder is an optical linear encoder having:

a code strip mounted to one of said first transducer assembly and said second transducer assembly, said code strip having a predetermined number of lines per inch; and an optical encoder module mounted to other of said first transducer assembly and said second transducer assembly, said optical encoder module having a slot through which said code strip slides as said first transducer assembly and said second transducer assembly move, reading said lines as said optical encoder modules traverses said lines, and accordingly supplying signals indicative of said relative positions of and distance between said first transducer assembly and said second transducer assembly.

4. An apparatus as set forth in claim 1 wherein said controller controls said transducer drive mechanism to separate said first transducer assembly and said second transducer assembly to allow movement of said foot to and from a position between said first transducer assembly and said second transducer assembly without interference from said first transducer assembly and said second transducer assembly.

5. An apparatus as set forth in claim 1 wherein said controller controls and moves said position encoder to a known transducer separation zero.

6. An apparatus as set forth in claim 1 wherein said controller controls said transducer drive mechanism to separate said first transducer assembly and said second transducer assembly to a cleaning or standby position.

7. An apparatus as set forth in claim 1 wherein said controller controls said transducer drive mechanism to secure said first transducer assembly and said second transducer assembly in an off or shipping position.

8. An apparatus as set forth in claim 1 wherein said predetermined quality is dependent upon at least an attenuation of said ultrasonic signals received by said other of said first transducer and said second transducer relative to said ultrasonic signals transmitted by said one of said first transducer and said second transducer.

9. A method for performing ultrasonic bone analysis comprising the steps of:

placing a patient's foot in a foot well of a foot well assembly to rest said foot;

securing a position of said foot in said foot well and a position of a lower leg of said patient using a shin guide assembly having a shin restraint section, an instep support section and a foot restraint section;

positioning a first transducer assembly and a second transducer assembly to apply a pressure against a heel of said patient which thereby achieves ultrasonic coupling;

transmitting ultrasonic signals using one of said first transducer assembly and said second transducer assembly;

receiving said transmitted ultrasonic signals using other of said first transducer assembly and said second transducer assembly;

determining a quality of said received ultrasonic signals;

comparing said quality of said received ultrasonic signals with a predetermined quality;

calculating a movement of said first transducer assembly and said second transducer assembly which would modify said coupling pressure to achieve said predetermined quality;

moving said first transducer assembly and said second transducer assembly according to said calculated movement; and repeating said transmitting, receiving, determining, comparing, calculating and moving steps until said quality of said received ultrasonic signals is not less than said predetermined quality.

10. A method As set forth in claim 9 wherein said securing step includes securing a strap of said shin restraint section around a calf of said patient.

11. A method as set forth in claim 10 further comprising the step of:

mechanically coupling said foot well assembly and said shin guide assembly by connecting first mating means of said foot well assembly with second mailing means of said shin guide assembly.

12. A method as set forth in claim 9 wherein said mechanically coupling step includes positioning said shin restraint section o f said shin guide assembly to for m a 95-degree angle relative to a bottom of said foot well.

13. A method as set forth in claim 9 wherein said transmitting step includes guiding said ultrasound signals using a coupling pad and an acoustical delay line of said one of said first transducer assembly and said second transducer assembly to collimate an acoustical beam a sufficient distance along a propagation axis to allow wavefronts to evolve onto a more uniform intensity pattern.

14. A method as set forth in claim 9 further comprising a step of applying a non-aqueous coupling gel between said heel of said patient and elastomer coupling pads of said first transducer assembly and said second transducer assembly, respectively, to more efficiently couple ultrasonic energy.

15. A method as set forth in claim 9 further comprising the steps of:

determining a distance between said first transducer assembly and said second transducer assembly using a position encoder; and calculating a speed of ultrasonic signals through said foot using said determined distance between said first transducer assembly and said second transducer assembly.

16. A method as set forth in claim 9 further comprising the step of separating said first transducer assembly and said second transducer assembly to allow movement of said foot to and from a position between said first transducer assembly and said second transducer assembly without interference from said first transducer assembly and said second transducer assembly.

17. A method as set forth in claim 9 further comprising the step of moving said position encoder to a known transducer separation zero.

18. A method as set forth in claim 9 further comprising the step of separating said first transducer assembly and said second transducer assembly to a cleaning or standby position.

19. A method as set forth in claim 9 further comprising the step of securing said first transducer assembly and said second transducer assembly in an off or shipping position.

* * * * *